United States Patent
Brazzell

(10) Patent No.: US 8,158,669 B2
(45) Date of Patent: Apr. 17, 2012

(54) METHOD FOR TREATING NEOVASCULARIZATION

(75) Inventor: Romulus K Brazzell, Alpharetta, GA (US)

(73) Assignee: QLT, Inc., Vancouver (CA)

( * ) Notice: Subject to any disclaimer, the term of this patent is extended or adjusted under 35 U.S.C. 154(b) by 850 days.

(21) Appl. No.: 11/975,325

(22) Filed: Oct. 18, 2007

(65) Prior Publication Data

US 2008/0096865 A1 Apr. 24, 2008

Related U.S. Application Data

(63) Continuation of application No. 11/484,473, filed on Jul. 11, 2006, now abandoned, which is a continuation of application No. 09/814,572, filed on Mar. 22, 2001, now abandoned.

(60) Provisional application No. 60/191,807, filed on Mar. 24, 2000.

(51) Int. Cl.
*A01N 43/38* (2006.01)
*A61K 31/40* (2006.01)

(52) U.S. Cl. ..................... 514/410; 424/9.61

(58) Field of Classification Search .............. 604/20, 604/289, 290; 424/9.61; 514/44, 211.08, 514/252.03, 410, 414
See application file for complete search history.

(56) References Cited

U.S. PATENT DOCUMENTS

| | | | | |
|---|---|---|---|---|
| 4,883,790 | A | 11/1989 | Levy et al. | 540/145 |
| 4,920,143 | A | 4/1990 | Levy et al. | 514/410 |
| 5,095,030 | A | 3/1992 | Levy et al. | 514/410 |
| 5,214,036 | A | 5/1993 | Allison et al. | 514/185 |
| 5,283,255 | A | 2/1994 | Levy et al. | 514/410 |
| 5,707,608 | A | 1/1998 | Liu | 424/9.61 |
| 5,756,541 | A | 5/1998 | Strong et al. | 514/502 |
| 5,770,619 | A * | 6/1998 | Richter et al. | 514/410 |
| 5,798,349 | A | 8/1998 | Levy et al. | 514/185 |
| 6,074,666 | A | 6/2000 | Desai et al. | 424/450 |
| 6,117,862 | A | 9/2000 | Margaron et al. | 514/185 |
| 6,214,819 | B1 * | 4/2001 | Brazzell et al. | 514/211.08 |
| 6,271,233 | B1 | 8/2001 | Brazzell et al. | 514/249 |
| 6,297,228 | B1 * | 10/2001 | Clark | 514/177 |
| 2002/0040015 | A1 * | 4/2002 | Miller et al. | 514/185 |
| 2003/0175282 | A1 | 9/2003 | Miller et al. | 424/155.1 |

FOREIGN PATENT DOCUMENTS

| | | |
|---|---|---|
| WO | 97/33619 | 2/1997 |
| WO | 99/03503 | 1/1999 |
| WO | 00/37107 | 12/1999 |
| WO | 01/51087 | 1/2001 |
| WO | 01/58240 | 2/2001 |

OTHER PUBLICATIONS

Casey et al., Pharmacology, Chapter 94, "Ocular Angiogenesis", pp. 1100-1105.
Ozaki et al., American Journal of Pathology, vol. 156, No. 2, "Blockade of Vascular Endothelial Cell Growth Factor Receptor Signaling is Suffucient to Completely Prevent Retinal Neovascularization", pp. 697-707, (Feb. 2000).
Seo et al., American Journal of Pathology, vol. 154, No. 6, "Dramatic Inhibition of Retinal and Choroidal Neovascularization by Oral Administration of a Kinase Inhibitor", pp. 1743-1753, (Jun. 1999).
Investigative Ophthalmology and Visual Science, vol. 42, No. 4, "Antiangiogenesis: Experimental and Clinical Paper Presentation", pp. S521-S522, (Mar. 15, 2001).
Ciulla et al., Exp. Opin. Invest. Drugs, vol. 8(12), "Changing therapeutic pardigms for exudative age-related macular degeneration: antiangiogenic agents and photodynamic therapy," pp. 2173-2182, (1999) [XP-0000978671].
Ferrario et al., Cancer Research, vol. 60, "Antiangiogenic Treatment Enhances Photodynamic Therapy Responsiveness in a Mouse Mammary Carcinoma." pp. 4066-4069, (Aug. 1, 2000).
nternational Search Report.
Dimitroff et al. "Anti-angiogenic activity of selected receptor tyrosine kinase inhibitors PD166285 and PD173074: Implications for combination treatment with photodynamic therapy," Investigational New Drugs 17 : 121-135 (1999).
McMillan et al. "Tumor growth inhibition and regression induced by photothermal vascular targeting and angiogenesis inhibitor retinoic acid," Cancer Letters 137: 35-44 (1999).
Renno et al. "Photodynamic Therapy Using Lu-Tex Induces Apoptosis in Vitro, and Its Effect Is Potentiated by Angiostatin in Retinal Capillary Endothelial Cells," Investigative Opthamology & Visual Science 41(12): 3963-3971 (2000).
Mohammadi et al., "Crystal structure of an angiogenesis inhibitor bound to the FGF receptor tyrosine kinase domain", The EMBO Journal, vol. 17, No. 20, pp. 5896-5904, (1998).
The Eyetech Study Group, "Anti-vascular Endothelial Growth Factor Therapy for Subfoveal Choroidal Neovascularization Secondary to Age-related Macular Degeneration," Ophthalmology (2003) 110(5):979-986.

* cited by examiner

*Primary Examiner* — Theodore Stigell
(74) *Attorney, Agent, or Firm* — Morrison & Foerster LLP

(57) ABSTRACT

The present invention describes an improved photodynamic treatment to treat subfoveal choroidal neovascularization (CNV).

7 Claims, No Drawings

METHOD FOR TREATING NEOVASCULARIZATION

This is a continuation of application Ser. No. 11/484,473 filed on Jul. 11, 2006, which is a continuation of application Ser. No. 09/814,572 filed on Mar. 22, 2001, which claims benefit of provisional Application 60/191,807 filed on Mar. 24, 2000, the entire disclosures of which are hereby incorporated by reference.

This application claims priority under 35 U.S.C. §119(e) from provisional patent application Ser. No. 60/191,807, filed Mar. 24, 2000, the entire disclosure of which is incorporated by reference herein in its entirety.

FIELD OF THE INVENTION

The invention relates to an improved method to treat ocular neovascularization, such as subfoveal choroidal neovascularization (CNV) by use of an anti-angiogenic agent as an adjunct to photodynamic therapy (PDT).

BACKGROUND OF THE INVENTION

The present treatment of age related macular degeneration (AMD) with photodynamic therapy using an appropriate photosensitive agent leads to excellent short-term results for treating CNV and is a significant improvement over laser photocoagulation. However, it has been demonstrated that in patients treated with PDT there can be a recurrence of choroidal neovascularization within the treatment area and/or development of new lesions outside the original lesions (so called progression) such that repeated PDT is required. Therefore a treatment regimen which could be used in conjunction with PDT, and which would prevent the growth of new vessels, would be advantageous for the treatment of CNV. The prevention of new, unwanted neovasculature could reduce the number of PDT treatments required in some subjects. The methods of the invention can also be used to treat other types of ocular tissue afflicted with neovascularization, such as retinal neovascular lesions due to, e.g., diabetes.

SUMMARY OF THE INVENTION

Accordingly, the present invention relates to a method for treating unwanted neovasculature in a subject, comprising:
(a) administering an effective amount of an anti-angiogenic agent to the subject;
(b) administering an effective amount of a photosensitive agent to the subject; and
(c) irradiating the unwanted neovasculature with light having a wavelength absorbable by the photosensitive agent.

In another aspect, the invention relates to a kit comprising at least one anti-angiogenic agent and at least one photosensitive agent.

DETAILED DESCRIPTION OF THE INVENTION

It has now been found that administration of an anti-angiogenic can be used in conjunction with PDT for the treatment of a subject having unwanted ocular neovasculature, e.g. CNV.

PDT as a treatment is well known in the art, and generally involves the use of a photosensitive agent activated by a laser. Preferred methods and compositions for PDT treatment of neovascularization utilizing a photosensitive agent and laser treatment is disclosed in U.S. Pat. Nos. 4,920,143; 5,095,030; 5,214,036; 5,707,608; 6,074,666; 5,770,619; 5,798,349; 5,756,541; 4,883,790; and 5,283,255, all of which are expressly incorporated by reference herein in their entirety. When PDT is employed to treat ocular neovascularization, the photosensitive agent lodges in the ocular tissue affected by neovascularization (i.e., the target ocular tissue) and is activated by a laser having a wavelength absorbable by the photosensitive agent. In the present invention, an anti-angiogenic agent is administered before, after and/or simultaneously with the photosensitive agent used in the PDT treatment. The combination of PDT and anti-angiogenic agent is referred to herein as "adjunctive PDT".

As used herein, the term "in conjunction with" is to be construed as administration of an anti-angiogenic agent to a subject either sequentially or simultaneously with a photosensitive agent, with the preferred method being sequential administration. As an example of sequential treatment, an anti-angiogenic agent may be administered between about 0 and about 4 weeks, more preferably between about 0.5 and about 1.5 weeks, before administration of the photosensitive agent. In an alternative sequential treatment, the anti-angiogenic agent may be administered between about 0 and about 4 weeks, more preferably between about 0 and about 1 week, after administration of the photosensitive agent. If necessary, the anti-angiogenic agent may be sequentially administered both before and after PDT according to the schedule described above. Alternatively, the treatment is considered simultaneous if the anti-angiogenic is co-administered with the photosensitive agent. Particular subjects may require multiple adjunctive PDT treatments. Particular adjunctive PDT treatments may require multiple administrations of the anti-angiogenic agent before PDT, multiple administrations of anti-angiogenic agent after PDT, or both.

Anti-angiogenic agents, as the term is used herein, mean agents that work by preventing, inhibiting or reversing the growth of new blood vessels via the process commonly known as angiogenesis. Examples of anti-angiogenic agents useful in adjunctive PDT include staurosporins, for example N-benzoyl-staurosporine, somatostatins, such as octreotide (D)Phe-Cys-Phe-(D)Trp-Lys-Thr-Cys-Thr-o, and steroids, such as triamcinolone. Other anti-angiogenic agents useful in the present invention are VEGF inhibitors, such as CGP 79987D, CGP 57 148B or CGP 53 716,

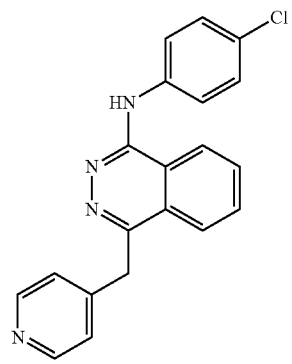

CGP 79787D

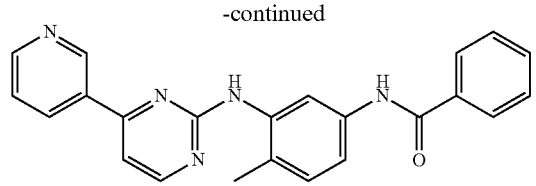

CGP 53'716

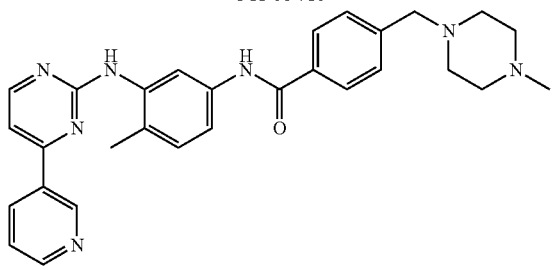

CGP 57'148 and the like. These anti-angiogenic agents are particularly useful to inhibit the recurrence, re-opening, development and/or progression of blood vessel growth that occurs during choroidal neovascularization, and offer significant benefits in adjunctive PDT.

Preferred anti-angiogenic agents are inhibitors of protein kinase C (PKC) (e.g., N-benzoyl-staurosporine), antagonists of growth hormone and IGF-1 (e.g., octreotide), antagonists of vascular endothelial growth factor (VEGF) (e.g., CGP 79787, N-benzoyl-staurosporine, CAM 781), inhibitors of cyclooxygenase II (e.g., diclofenac, rofecoxib, celecoxib, and the like), antagonists of angiotensin II (e.g., valsartan), antagonists of NF-kappa B, and PLA2 antagonists. More preferred anti-angiogenic agents are PKC inhibitors, VEGF antagonists and antagonists of growth hormone and IGF-1.

Most preferred anti-angiogenic agents are inhibitors of PKC and antagonists of VEGF, in particular inhibitors of PKC, such as N-benzoyl-staurosporine, CGP 79787, and octreotide. Particularly preferred is N-benzoyl-staurosporine.

Preferred photosensitive agents are the chlorins, bacteriochlorins, phthalocyanines, porphyrins, purpurins, merocyanines, pheophorbides and psoralens.

Highly preferred photosensitive agents are the porphyrins and is most preferably the a green porphyrin, in particular benzoporphyrin derivative monoacid ring A ("BPD-MA").

Any of the photosensitive compounds described above can be used in the methods of the invention. Of course, mixtures of two or more photosensitive compounds can also be used; however, the effectiveness of the treatment depends on the absorption of light by the photosensitive compound so that if mixtures are used, components with similar absorption maxima are preferred.

The nature of the formulation used to deliver the anti-angiogenic agent or photosensitive agent will depend in part on the mode of administration and on the nature of the anti-angiogenic agent and the photosensitive agent selected. Any pharmaceutically acceptable excipient, or combination thereof, appropriate to the particular active compounds may be used. Thus, the photosensitive agents or anti-angiogenic compounds may be administered as an aqueous composition, as a transmucosal or transdermal composition, as a subtenons or intraocular injection or in an oral formulation. The formulation may also include liposomes. Liposomal compositions are particularly preferred especially where the photosensitive agent is a green porphyrin. The anti-angiogenic agent is preferably administered via an aqueous carrier.

The above mentioned anti-angiogenic agents can be administered in any of a wide variety of ways, for example, orally, parenterally, or rectally, or the compound may be placed directly in or on the eye. Parenteral administration, such as intravenous, intramuscular, or subcutaneous, is preferred for the photosensitive agent. Intravenous injection is especially preferred. Oral administration or ocular administration is preferred for administration of the anti-angiogenic agent.

The dose of the above compounds can vary widely depending upon the mode of administration; the formulation in which it is carried, such as in the form of liposomes, or whether it is coupled to a target-specific ligand, such as an antibody or an immunologically active fragment. As is generally recognized, there is a nexus between the type of photosensitive agent, the formulation, the mode of administration, and the dosage level. The anti-antigenic agent is administered in a manner and amount sufficient to effect agent interaction with the unwanted neovasculature. The photosensitive agent is administered in an amount effective to close or eradicate the unwanted neovasculature upon irradiation with light of the appropriate wavelength.

While various photoactive compounds require different dosage ranges, if green porphyrins are used, a typical dosage is of the range of 0.1-50 mg/m$^2$ of body surface area, preferably from about 1-10 mg/m$^2$ and even more preferably about 2-8 mg/m$^2$.

While various anti-angiogenic compounds require different dosage ranges, a typical dosage is of the range of 1-500 mg/kg of body weight, preferably from about 10-250 mg/kg of body weight.

The irradiation (laser power, irradiation duration) is carried out in accordance to methods known in the art as mentioned above, for example in accordance to the light treatment protocols set out in U.S. Pat. Nos. 5,770,619; 5,798,349; 5,756,541; 4,883,790; and 5,283,255.

Kits that contain an anti-angiogenic agent and a photosensitive agent are also within the scope of the invention. Such kits can also contain suitable vehicles for the reconstitution or administration of the aforesaid anti-angiogenic agents as well as devices for the administration of such agents.

What is claimed is:

1. A method for treating unwanted ocular neovasculature in a subject suffering from choroidal neovascularization or retinal neovascularization, the method comprising;
    (a) administering an effective amount of a photosensitive agent to the subject; and
    (b) irradiating the unwanted neovasculature with light having a wavelength absorbable by the photosensitive agent, followed by
    (c) administering an effective amount of an antagonist of vascular endothelial growth factor (VEGF).

2. The method of claim 1, wherein the antagonist of VEGF is administered between 0 and about 4 weeks after the administration of the photosensitive agent.

3. The method of claim 2, wherein the antagonist of VEGF is administered between about 0.5 and about 4 weeks after administration of the photosensitive agent.

4. The method of claim 1, wherein the photosensitive agent is selected from the group consisting of a porphyrin and a purpurin.

5. The method of claim 4, wherein the photosensitive agent is benzoporphyrin derivative monoacid ring A.

6. The method of claim 1, wherein multiple administrations of the antagonist of VEGF are performed after the administration of the photosensitive agent.

7. The method of claim 1 wherein the subject is suffering from retinal neovascularization.

* * * * *